United States Patent [19]

Butte, Jr. et al.

[11] 4,271,089
[45] Jun. 2, 1981

[54] CYANOALKYLATION PROCESS

[75] Inventors: Walter A. Butte, Jr., West Chester; Wesley R. Cherry, Prospect Park, Pa.

[73] Assignee: Suntech, Inc., Philadelphia, Pa.

[21] Appl. No.: 54,771

[22] Filed: Jul. 5, 1979

Related U.S. Application Data

[63] Continuation-in-part of Ser. No. 916,393, Jun. 16, 1978, abandoned.

[51] Int. Cl.$^3$ .......................................... C07C 120/00
[52] U.S. Cl. ............................... 260/465.6; 260/464; 260/465 R; 260/465 D; 260/465 E; 260/465 F; 260/465.1; 260/465.4; 260/465.5 R; 260/465.8 R
[58] Field of Search ............. 260/464, 465.1, 465.5 R, 260/465.6, 465.8 R, 465 F

[56] References Cited

U.S. PATENT DOCUMENTS

| | | | |
|---|---|---|---|
| 2,382,036 | 8/1945 | Bruson | 260/465.6 |
| 2,579,580 | 12/1951 | Howk et al. | 260/464 |
| 2,770,640 | 11/1956 | Journeay | 260/465.6 |
| 2,809,988 | 10/1957 | Heininger | 260/465.6 |
| 2,853,510 | 9/1958 | Montagna et al. | 260/465.6 |
| 3,150,142 | 9/1964 | Eby | 260/465.1 X |
| 3,324,164 | 6/1967 | Merkel et al. | 260/464 |
| 3,701,802 | 10/1972 | Maerker et al. | 260/404 |
| 3,914,280 | 10/1975 | Yamakami et al. | 260/465.5 R |
| 3,957,848 | 5/1976 | Reedy et al. | 260/465.6 |

FOREIGN PATENT DOCUMENTS

| | | |
|---|---|---|
| 1054685 | 1/1967 | United Kingdom . |
| 1435063 | 5/1976 | United Kingdom . |

OTHER PUBLICATIONS

Kirk–Othmer, "Encyclopedia of Chemical Technology", 2nd ed., vol. 6, 1965, pp. 634–664.
Bruson, Chemical Reactions, vol. 5, 1949, pp. 79–113.

*Primary Examiner*—Joseph Paul Brust
*Attorney, Agent, or Firm*—J. Edward Hess; Donald R. Johnson; Anthony Potts, Jr.

[57] ABSTRACT

In a cyanoalkylation process involving the reaction of a cyanoalkene compound such as acrylonitrile with a compound containing a labile hydrogen such as ethylene glycol, to form a cyanoalkylated product such as 3,3'-ethylenedioxy-bis(propionitrile), the reaction is carried out in the presence of cyanoalkylated product in addition to the cyanoalkylated product which is formed in situ by reaction of the reactants. High yields of cyanoalkylated product and low formation of by-products are obtained.

11 Claims, 1 Drawing Figure

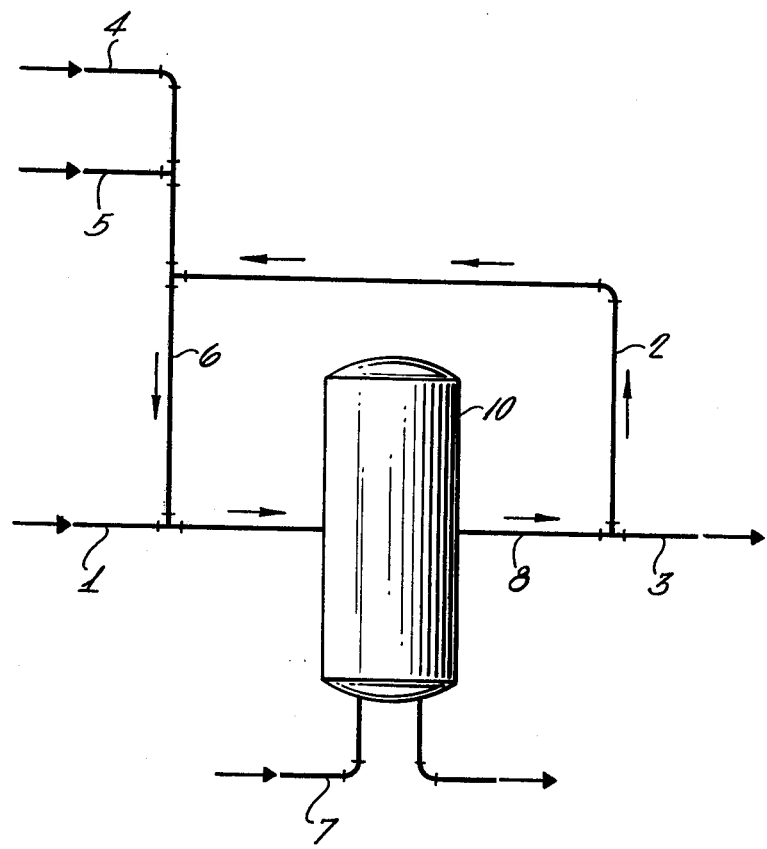

CYANOALKYLATION PROCESS

CROSS REFERENCE TO RELATED APPLICATIONS

The subject matter of this application is a continuation-in-part of U.S. Pat. application Ser. No. 916,393, filed June 16, 1978 by the above-identified applicants, now abandoned.

BACKGROUND

This invention is directed to an improvement in cyanoethylation and other cyanoalkylation processes. The process involved is preferably continuous, although it may also be performed in batch operations. The invention will be further described with reference to cyanoethylation processes, but it is understood that the invention is also useful in connection with other cyanoalkylation processes as further disclosed herein.

Cyanoethylation refers to the reaction between acrylonitrile and a variety of compounds of yield $\beta$-substituted propionitrile derivatives. The compounds are characterized by their possession of a labile hydrogen atom. The latter is a hydrogen atom bonded to an electronegative atom or to an atom activated by strongly electronegative substituents. Classes of compounds containing labile hydrogen include those having hydroxyl groups, e.g., alcohols and glycols. Cyanoethylation can be generalized by the following reaction formula:

For alcohols the reaction is as follows:

For polyalcohols the reaction can be considered as a two step reaction, thus:

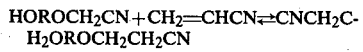

Cyanoethylation is used in the formation of a great variety of mono- and poly-functional nitriles, for examples see *Encyclopedia of Chemical Technology*, Kirk-Othmer, 2nd Edition, Volume 6, and *Organic Reactions*, R. Adams et al., Vol. 5, John Wiley and Sons, N.Y. 1949. Cyanoethylation products are useful intermediates for the manufacture of plastics and fibers.

For large scale production of $\beta$-substituted propionitrile derivatives, it is advantageous, particularly in a continuous process, to operate the cyanoethylation reaction with rapid mixing of the reactants. However, this is difficult to do while obtaining economically high yields because: (1) the cyanoethylation reaction is highly exothermic; (2) the acrylonitrile tends to polymerize when present in high concentrations; and (3) the cyanoethylation reaction is readily reversible at certain conditions. To avoid the foregoing problems it is possible to add slowly the acrylonitrile to an excess amount of the compound containing the labile hydrogen atoms. But the latter is relatively inefficient since long residence times are required to attain a high level of conversion.

Overcoming the aforementioned problems is the present invention which is an improvement to the cyanoethylation process. The improvement permits the cyanoethylation to be carried out in a controlled manner and with high yields of $\beta$-substituted propionitrile derivatives. The high yields are surprising since the cyanoethylation reaction is known to be readily reversible under typical operating conditions. The improvement also eases the problem of heat removal. Further, the improvement reduces, if not eliminates, the need for an inert solvent.

U.S. Pat. No. 3,324,164 to Merkel et al. discloses a reaction of acrylonitrile with monohydric or polyhydric alcohols in a series of reactors with simultaneous supply of reactants to the separate reactors and with intense mixing of reactants in each reactor. This mixing is obtained for example by circulation of liquid from the bottom of the reactor to the top of the reactor at a rate of 10 to 1,000 times the rate of supply to or withdrawal from the reactor of the reactants. There is no suggestion in this patent of any desirability of recirculating liquid when intense mixing is obtained by other means such as the use of stirring means, blowing in inert gas, etc. Nor is there any suggestion of recirculating liquid at lower rates which do not result in intense mixing.

U.S. Pat. No. 2,579,580 to Howk et al. discloses reaction of acrylonitrile with various compounds such as water, aldehydes and ketones using a solid resin catalyst. To obtain intimate contact between liquid reactants and solid catalyst, the mixture is stirred, or the liquid mixture is recirculated until a satisfactory yield of reaction product is obtained. Similarly to the Merkel et al. patent, there is no suggestion in this patent of recirculating liquid when mixing is obtained by other means, nor of recirculating liquid at low rates which do not result in intense mixing. Nor is there any suggestion of recirculating liquid when a satisfactory yield of product is obtained in a single pass.

Various patents disclose reaction of acrylonitrile with compounds having labile hydrogen atoms, separation of the desired reaction products from material which is desired to be further reacted, and recycle of the latter to the reactor. Such patents do not however suggest recycling a portion of the entire reactor effluent, containing desired reaction products as well as unreacted or partially reacted materials. Typical of such patents are U.S. Pat. Nos. 2,382,036; 2,809,988; 2,853,510 and 3,914,280.

Various additional patents disclose reaction of acrylonitrile with compounds having labile hydrogen atoms, but without any disclosure of recycling a portion of the entire reactor effluent containing desired reaction products. Typical of such patents are U.S. Pat. Nos. 2,280,790; 2,404,164; 2,770,640; 3,150,142; 3,701,802 and 3,957,848; and British Pat. No. 544,421.

SUMMARY OF THE INVENTION

According to present invention, a cyanoalkene and a labile hydrogen compound are reacted in the presence of cyanoalkylated product in addition to that which is formed in situ by the reaction. Typically, such additional cyanoalkylated product is provided in the reaction zone by recycling to the reaction zone a portion of the cyanoalkylated product produced in the reaction. Such operation has been found to reduce substantially the amount of unwanted by-products such as cyanoalkene polymer.

BRIEF DESCRIPTION OF THE DRAWING

The accompanying FIGURE is a schematic drawing of one embodiment of the improvement in the continuous cyanoethylation process.

EMBODIMENTS

The invention will be futher described with reference to the reaction of acrylonitrile with ethylene glycol, to form a diadduct such as 3,3′-ethylene dioxybis (propionitrile), $CNCH_2CH_2OCH_2CH_2OCH_2CH_2CN$, but it is understood that the invention is also useful in connection with other cyanoalkylation processes as further disclosed herein.

In the accompanying FIGURE the acrylonitrile feed (1) is introduced into reaction means (10). Accompanying the feed acrylonitrile (1) is stream (6) whose components are a compound containing a labile hydrogen i.e., ethylene glycol (4), a catalyst (5), if used and a recycle (2) which is a portion of the reactor effluent (8). The balance of the reactor effluent (3) is processed to separate the desired β-substituted propionitrile derivatives from any unreacted acrylonitrile, by-products, reactant intermediates, and catalyst, if used.

Reaction means (10) is designed to provide a residence time for the reactants, catalyst, if used, and product which results in a desired conversion. Means (10) also can contain means (not shown) for mixing the contacting materials. Means (10) also can contain optional means (7) for cooling the cyanoethylation reaction. Generally the residence time will range between from about a quarter of an hour to about five to seven hours. Another way of indicating residence time is the composition of the effluent. Generally the effluent leaving the cyanoethylation reaction zone contains less than 3 wt. % unreacted acrylonitrile and preferably less than 1 wt. %. Another measure of residence time is the amount of desired product in the effluent. Generally the effluent contains at least 90 wt. % of the desired product, i.e., the cyanoethylated product, and preferably at least 95 wt. %.

As can be seen in the FIGURE the reaction effluent is divided into a portion which constitutes an amount in the range between from about 50 wt. % to about 90 wt. % and includes product. The divided portion is recycled back to reaction zone (10) as indicated.

The ratio of added cyanoalkylated product to feed reactants, i.e., cyanoalkene and labile hydrogen compound, is preferably in the range from about 1 to about 9 volumes, more preferably about 1.5 to about 4 volumes of added cyanoalklated product to 1 volume of reactants. Generally any amount of added product sufficient to avoid excessive formation of by-products can be used. The amount of by-products which can be tolerated can vary from case to case, but usually the amount formed will not exceed 5 wt. %, and typically will not exceed 3 wt. %, more preferably not exceed 1 wt. % of the reaction product mixture. The amount of added product used will generally not exceed the amount which reduces the formation of by-products to a desired level, since using greater amounts of added product increases the cost of the operation.

The addition of cyanoalkylated product according to the invention permits the reaction to be carried out with rapid addition of the cyanoalkene to the reaction mixture, while still avoiding excessive formation of undesired by-products. In the absence of the added product, rapid addition of cyanoalkene results in rapid temperature rise and excessive by-product formation.

The process of the invention is applicable generally to any process for reaction of cycloalkenes and labile hydrogen compounds. Such processes are well known and can be carried out noncatalytically in some cases, or catalytically with various catalysts such as disclosed, for example, in the aforementioned encyclopedia. The catalyst can be liquid or solid, e.g., ion exchange resin, and can, if a suitable liquid, form a homogeneous mixture with the reactants and products. The contacting can be batch or continuous.

The temperature employed in the process is usually in the range from about 0° C. to about 100° C., preferably about 20° C. to 80° C., but any known cyanoalkylation temperature can be employed. The process can be carried out with cooling of the reaction zone, e.g., by indirect heat exchange, in order to prevent excessive temperature rise and the formation of unwanted by-products. However, the process of the present invention, by adding cyanoalkylated product to the reaction mixture, controls temperature and avoids unwanted by-products without the necessity for means to remove larger amounts of heat from the reaction zone rapidly.

The cyanoalkylation product, e.g., the diadduct of acrylonitrile and ethylene glycol, which is added to the reaction mixture according to the present invention seems to be an inert material in the reaction. It may have associated with it some partially reacted material such as the monoadduct of acrylonitrile and ethylene glycol. The monoadduct can undergo further reaction when introduced into the reaction mixture as in the case of recycling to the reaction zone of effluent material comprising mainly the diadduct but also some monoadduct.

Cyanoalkenes which may be employed in the process of the invention are those which undergo cyanoalkylation reactions. The most common such cyanoalkene is acrylonitrile. Others which may be employed include crotononitrile, alpha-methylacrylonitrile beta-vinylacrylonitrile, and others known to those skilled in the art.

In related U.S. application Ser. No. 916,394, filed June 16, 1978 by the present inventors, the conversion of cyanoalkenes in a cyanoalkylation reaction is limited to not more than about 96%, in order to avoid formation of unwanted by-products. The process of the present invention permits conversions greater than 96% without excessive formation of unwanted by-products. Usually the process of the invention converts at least 90% of the cyanoalkene, and preferably at least 97%, but lower amounts are within the scope of the invention.

As is known a strongly basic catalyst is often used for the cyanoethylation reaction; however, it does depend on which particular compound containing a labile hydrogen atom is used. Thus for example a strongly basic catalyst is used an aliphatic monohydric or polyhydric alcohol whereas no catalyst is used if the compound is a primary or secondary aliphatic amine. Furthermore, as is known, acids act as catalysts under certain circumstances. The quantity of catalyst required is small. In general 1–5 wt. % of catalyst based on the weight of acrylonitrile is satisfactory. Useful catalysts include alkali metals, oxides of alkali metals, and hydroxides of alkali metals. Often the hydroxide of the alkali metals, e.g., KOH and NaOH, is a concentrated aqueous solution.

As stated heretofore, one of the reactants in the cyanoethylation reaction is a compound containing a labile hydrogen atom. Thus the reaction can be effected with compounds having one or more —NH— groups, such as primary and secondary amines, lactams, amides; compounds having one or more —OH— or —SH groups such as monohydric or polyhydric alcohols (e.g., the aliphatic polyhydric alcohols, ethylene glycol, diethylene glycol, propylene glycol, 1,4-butylene glycol, 1,2-cyclohexane diol), water, phenols, mercaptans; —CH—, —CH$_2$— or —CH$_3$ group contiguous to the carbonyl groups; compounds having a methylene group activated by various radicals such as —CN (e.g., benzyl cyanide), —NO$_2$ (e.g., nitropropane), —COOH or —COOR (e.g., malonic esters), the ethylenic carbons of a carbocycle or heterocycle (e.g., cyclopentadiene, indene); and the like. Any organic compound susceptible of undergoing cyanoethylation may be used in the process of this invention.

The cyanoethylation process can also be described as follows. Acrylonitrile (1) at the rate of 613 pounds per hour is injected into means (10). Just prior to the injection into means (1), ethylene glycol (4), at a rate of 358 pounds per hour, into which is injected sodium hydroxide (5) at a rate of 29 pounds per hour, is injected into the acrylonitrile (1). Also contacting the ethylene glycol and sodium hydroxide mixture is 2000 pounds of reactor effluent (2) and the resulting three component mixture contacts the acrylonitrile (1). The product mixture (3), at a rate of 1000 pounds per hour is withdrawn from the system. The product mixture (3) is sent to purification means where the catalyst is neutralized and the desired product is separated, e.g., by distillation. The neutralized and separated product consists of essentially 3,3'-ethylene-dioxybis(propionitrile), e.g., in excess of 95 wt. %. The yield of the product is in excess of 95 wt. % based on the ethylene glycol (4) and acrylonitrile charged to the reaction means (10).

Thus the improvement for cyanoalkylation of an organic compound having a labile hydrogen atom involves the following. In conventional practice, cyanoalkylation involves contacting the organic compound at a cyanoalkylation temperature with a cyanoalkene and a cyanoalkylation catalyst in a reaction zone. The conventional practice has the disadvantage in that the reaction tends to be accompanied by undesired reactions with a resulting reduction in selectivity for the desired cyanoalkylation product. The improvement to the foregoing cyanoalkylation process comprises removing the reaction effluent from the reaction zone, and dividing it to obtain a portion thereof, which is recycled to the reaction zone to contact additional amounts of the organic compound, the cyanoalkene and the catalyst, thereby reducing the production of unwanted reaction products.

The improvement can further comprise that the recycled portion of the reaction effluent contacts first a compound containing the labile hydrogen atoms and the resulting mixture of the two contacts acrylonitrile. The latter is fresh acrylonitrile which is fed to the reaction zone. The improvement further comprises that the resulting mixture of the recycled reactor effluent and the compound containing the labile hydrogen atom contacts a basic catalyst prior to contacting the acrylonitrile entering the reaction zone.

The following examples, along with a comparative run, illustrate the improvement.

EXAMPLE 1

In this example the cyanoethylation reaction was carried out continuously in a $\frac{1}{4} \times 84$ inch stainless steel tubular reactor immersed in a circulating bath regulated at 30° C. Ethylenedioxybis(propionitrile) was pumped at 0.247 ml/min. to a mixing-tee. There it merged with ethylene glycol containing 7 wt. % of 40% aqueous sodium hydroxide that was pumped at the rate of 0.0285 ml/min. The rate of ethylene glycol as such was 0.0299 gram per minute. The mixed stream was led through a $\frac{1}{4} \times 20$ inch tube to a second tee and acrylonitrile was pumped at 0.0741 ml/min., or 0.0599 gram per minute, i.e., 2.34 moles/mole glycol. This mixed stream entered the reactor directly and upon exiting was collected in a graduated receiver from which sample cuts were withdrawn periodically. The samples were neutralized by shaking with a sulfonic acid ion-exchange resin and then analyzed by gas chromatography.

A sample taken after 3 hours contained 93 wt. % dinitrile, 1 wt. % mononitrile and 1 wt. % by-products. The balance was water from the catalyst and excess acrylonitrile. This analysis corresponds to 98 wt. % selectivity to useful product. Selectivity refers to the amount by weight of acrylonitrile converted to mononitrile product plus the amount by weight of acrylonitrile converted to dinitrile product in proportion to the sum of those amounts and of the amount by weight of by-products formed. Another sample removed after 4 hours was virtually identical indicating that steady-state operation had been achieved.

EXAMPLE 2

In operation generally similar to that in Example 1, about 0.03 gram per minute of ethylene glycol, 0.06 gram per minute of acrylonitrile, and 0.26 gram per minute of ethylene dioxybis(propionitrile) are mixed and the ethylene glycol and acrylonitrile are reacted to produce about 0.08 gram per minute of ethylene dioxybis(propionitrile). Ethylene dioxybis(propionitrile) is removed from the reactor at a rate of about 0.34 gram per minute, of which about 77 percent or 0.26 gram per minute, is recycled to provide the ethylene dioxybis(propionitrile) charged to the reactor. The results are generally similar to those obtained in Example 1.

EXAMPLE 3

Another continuous reaction was performed in the same manner as described above except that the acrylonitrile was pumped at 0.0667 ml./min. or 0.0538 gram per minute, 2.1 moles/mole glycol. Samples taken after 3 and 4 hours of operation were analyzed as before. They contained 95-96 wt. % dinitrile, 0.5 wt. % mononitrile, 0.5-1.0 wt. % other by-products and 3-4 wt. % water plus residual acrylonitrile. The corresponding selectivity was 98-99 wt. %.

COMPARISON EXAMPLE

In contrast the following illustrates one of the problems, particularly of a rapid exotherm, that can develop during the cyanoethylation. To a 500 ml. Morton flask fitted with a stirrer, reflux condensor and an additional funnel and immersed in an ice water bath was added 62 g. of ethylene glycol and 5 g. of 40% aqueous NaOH. To the resulting mixture was rapidly added 106 g. of acrylonitrile from the funnel and then the stirrer was turned on. Within 5 minutes, the temperature rose to 60°

C. and then rapidly to 120° C. at which temperature the contents erupted from the flask.

To more clearly illustrate how the presence of reaction product can help control the exotherm problem the following run was made.

EXAMPLE 4

To a 2000 ml. flask fitted with a stirrer, reflux condensor and an additional funnel and immersed in an ice water bath was added 248 g. of ethylene glycol and 20 g. of 40% aqueous NaOH. The stirrer was started and the 424 g. of acrylonitrile was added from the funnel over a period of about 15 minutes. The temperature remained in the range of 25°–35° C. during the addition of the acrylonitrile. The stirring was continued for one additional hour after which 170 g. of the reaction mixture was withdrawn from the flask and neutralized by contacting with 70 g. of a sulfonic acid resin. The withdrawn mixture contained more than 95 wt. % of 3,3'-ethylenedioxy-bis(propionitrile), and essentially no acrylonitrile. This run was performed with gradual addition of acrylonitrile to produce the 3,3'-ethylenedioxy-bis(propionitrile) for use in the subsequent run with rapid addition of acrylonitrile.

The follwing were rapidly added to the foregoing flask containing the remaining reaction mixture and in the following order: Ethylene glycol, 62 g.; aqueous (40%) NaOH, 5 g.; and acrylonitrile, 106 g. The temperature remained at about 30° C. during the addition and the stirring was continued for 90 minutes. Afterward the contents of the flask were neutralized with sulfonic acid resin as described above. The composition of this second batch was virtually identical to the first withdrawn mixture in that it contained more than 95 wt. % of the propionitrile derivative and essentially no acrylonitrile.

The use of other compounds containing a labile hydrogen, e.g., ammonia, an amine, ethanol, propanol, 2-ethyl-1-hexanol, and the like, will yield analogous results. Also use of other cyanoalkenes, such as alpha-methylacrylonitrile and the like, will yield similar results.

We claim:

1. In a process for cyanoalkylation of a compound having a labile hydrogen atom selected from the group consisting of monohydric alcohol, polyhydric alcohol, water and phenol which comprises contacting said compound at a cyanoalkylation temperature with a cyanoalkene selected from the group consisting of acrylonitrile, alpha-methyl acylonitrile, crotononitrile, and beta-vinyl-acrylonitrile, and a cyanoalkylation catalyst in a reaction zone to form a cyanoalkylated product and by-products wherein the reaction is accompanied by undesired production of by-products with resulting reduction in selectivity for the desired cyanoalkylated product, the improvement which comprises conducting the reaction in the presence of about 1 to 9 volumes of the cyanoalkylated product in addition to that which is formed is situ by reaction of the compound and said cyanoalkene, whereby production of by-products is reduced.

2. Process according to claim 1 wherein a portion of effluent from the reaction zone is recycled to the reaction zone to provide the cyanoalkylated product.

3. Process according to claim 1 wherein the compound is an aliphatic polyhydric alcohol, and the desired cyanoalkylated product is a dinitrile.

4. Process according to claim 1 wherein the temperature in the reaction zone is maintained in the range between about 0° C. to about 100° C.

5. Process according to claim 1 wherein the cyanoalkylation catalyst is an aqueous solution of a hydroxide of an alkali metal.

6. Process according to claim 1 wherein reactor effluent contains more than about 90 wt. % of the cyanoalkylation product.

7. Process according to claim 6 wherein the reactor effluent further contains less than about 3 wt. % of unreacted cyanoalkene.

8. Process according to claim 7 wherein the temperature in the reaction zone is maintained in the range between from about 0° C. to about 100° C. and the cyanoalkylation catalyst is an aqueous solution of a hydroxide of an alkali metal.

9. Process according to claim 8 wherein the cyanoalkylated product is 3,3'-ethylene dioxybis(propionitrile).

10. In a process for cyanoethylation of ethylene glycol which comprises contacting the ethylene glycol, at a cyanoethylation temperature with acrylonitrile and a cyanoethylation catalyst in a reaction zone to form 3,3'-ethylene dioxybis(propionitrile), a monoadduct of acrylonitrile and ethylene glycol and by-products, wherein the reaction is accompained by undesired production of by-products with resulting reduction in selectivity for 3,3'-ethylene dioxybis(propionitrile), the improvement which comprises conducting the reaction in the presence of about 1 to 9 volumes of 3,3'-ethylene dioxybis(propionitrile), in addition to that which is formed in situ by reaction of the ethylene glycol and the acrylonitrile, whereby the production of the by-products is reduced.

11. In a process for cyanoethylation of an aliphatic polyhydric alcohol which comprises contacting the aliphatic polyhydric alcohol at a cyanoethylation temperature with acrylonitrile and a cyanoethylation catalyst in a reaction zone to form a polynitrile, other adducts of acrylonitrile and aliphatic polyhydric alcohol and by-products, wherein the reaction is accompanied by undesired production of by-products with resulting reduction in selectivity for the polynitrile the improvement which comprises conducting the reaction in the presence of about 1 to 9 volumes of the polynitrile in addition to that which is formed in situ by reaction of the aliphatic polyhydric alcohol and the acrylonitrile, whereby the production of the by-products is reduced.

* * * * *